United States Patent
Collier et al.

(10) Patent No.: US 12,015,870 B2
(45) Date of Patent: Jun. 18, 2024

(54) X-RAY ONSET DETECTOR FOR INTRAORAL DENTAL SENSOR

(71) Applicant: BAE Systems Imaging Solutions Inc., San Jose, CA (US)

(72) Inventors: Glen L. Collier, Morgan Hill, CA (US); Stephen W. Mims, San Diego, CA (US); George Y. Wang, San Jose, CA (US); Kun Zhao, Milpitas, CA (US); Stanley K. Searing, San Jose, CA (US)

(73) Assignee: BAE Systems Imaging Solutions Inc., San Jose, CA (US)

( * ) Notice: Subject to any disclaimer, the term of this patent is extended or adjusted under 35 U.S.C. 154(b) by 101 days.

(21) Appl. No.: 17/817,146

(22) Filed: Aug. 3, 2022

(65) Prior Publication Data

US 2024/0048667 A1   Feb. 8, 2024

(51) Int. Cl.
*H04N 5/32*      (2023.01)
*A61B 6/51*      (2024.01)
(Continued)

(52) U.S. Cl.
CPC ............ *H04N 5/32* (2013.01); *A61B 6/512* (2024.01); *H04N 25/50* (2023.01); *H04N 25/702* (2023.01); *H04N 25/75* (2023.01)

(58) Field of Classification Search
CPC ....... A61B 6/145; A61B 6/025; A61B 6/5205; A61B 6/14; A61B 6/587; A61B 2562/187;
(Continued)

(56) References Cited

U.S. PATENT DOCUMENTS 6,404,854 B1   6/2002   Carroll et al.
7,016,466 B2   3/2006   Rinaldi et al.
(Continued)

FOREIGN PATENT DOCUMENTS

EP      1337107 A2    8/2003

OTHER PUBLICATIONS

International Search Report, PCT/US23/28208, mailed Oct. 19, 2023, 8 pages.

*Primary Examiner* — Masum Billah
(74) *Attorney, Agent, or Firm* — Finch & Maloney PLLC; Gary McFaline

(57) ABSTRACT

Techniques are provided for x-ray onset detection for an intraoral dental sensor. A methodology implementing the techniques according to an embodiment includes calculating a plurality of superpixel values for each of a plurality of rows of detector pixels of a sensor. Each of the superpixel values is based on a sum of pixel values of a set of pixels associated with the superpixel value, the set of pixels selected from the detection row of a current frame of the sensor. The method also includes calculating a difference between each of the superpixel values and a corresponding stored superpixel value generated from a previous sensor frame and determining if the differences exceed a superpixel threshold value. The method further includes incrementing a hit counter in response to the determination and generating a detection signal if the hit counter exceeds a hit count threshold, otherwise proceeding to process the next detection row.

17 Claims, 7 Drawing Sheets

(51) Int. Cl.
  *H04N 25/50* (2023.01)
  *H04N 25/702* (2023.01)
  *H04N 25/75* (2023.01)

(58) Field of Classification Search
  CPC ....... A61B 6/4464; A61B 6/4488; A61B 6/56;
   A61B 6/08
  USPC ........................................................ 348/162
  See application file for complete search history.

(56) References Cited

U.S. PATENT DOCUMENTS

| | | |
|---|---|---|
| 7,755,056 B2 | 7/2010 | Bell |
| 8,119,990 B2 | 2/2012 | Zeller |
| 8,324,587 B2 | 12/2012 | Zeller |
| 8,481,956 B2 | 7/2013 | Boucly et al. |
| 9,492,129 B2 | 11/2016 | Zeller et al. |
| 9,907,521 B2 | 3/2018 | Papaix et al. |
| 10,230,906 B2 | 3/2019 | Topfer et al. |
| 2004/0228452 A1 | 11/2004 | Rinaldi et al. |
| 2007/0195935 A1 | 8/2007 | Vermeulen et al. |
| 2011/0013746 A1* | 1/2011 | Zeller .................... A61B 6/512 378/98 |
| 2016/0292876 A1 | 10/2016 | Zhao et al. |
| 2022/0175328 A1 | 6/2022 | Wieczorek et al. |

* cited by examiner

X-RAY ONSET DETECTOR FOR INTRAORAL DENTAL SENSOR

FIELD OF DISCLOSURE

The present disclosure relates to x-ray sensor systems, and more particularly, to an x-ray onset detector for an intraoral dental sensor.

BACKGROUND

X-ray imaging is frequently used in dental care to visualize features of tooth anatomy, including cavities or other defects that require attention and treatment. Originally, film was used to capture images generated by the relative attenuation of the x-ray radiation as it passed through different parts of the tooth. Later, electronic sensors came into use as a replacement for film and offered many advantages including faster access to the images (since the film development process was eliminated) and generally lower levels of radiation. It is generally desirable to avoid unnecessary radiation exposure whenever possible, and reliable detection of x-ray onset can be useful to improve patient safety and image quality.

Figure 1:
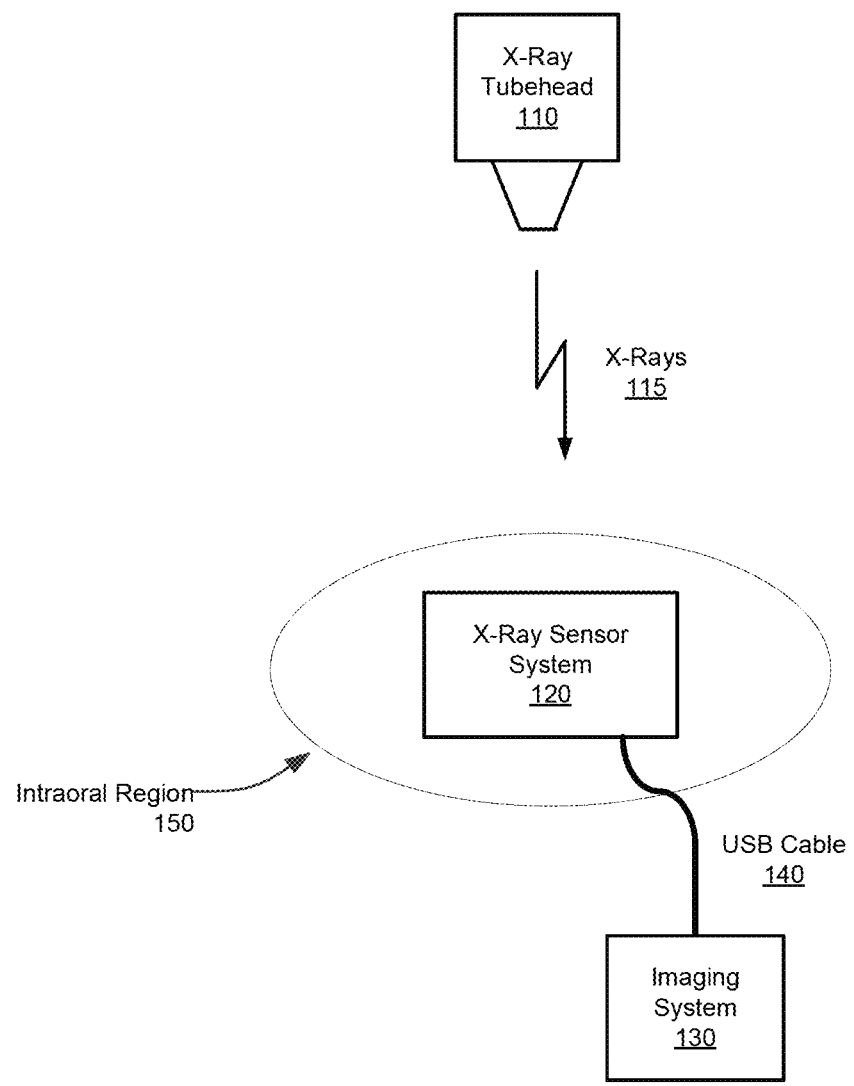
FIG. 1 illustrates an implementation of an x-ray sensor system for intraoral imaging, in accordance with an embodiment of the present disclosure.

Although the following Detailed Description will proceed with reference being made to illustrative embodiments, many alternatives, modifications, and variations thereof will be apparent to those skilled in the art.

DETAILED DESCRIPTION

Techniques are provided for implementing an x-ray onset detector for use with an intraoral dental sensor system. As noted previously, it is generally desirable to avoid unnecessary radiation exposure to the patient whenever possible. Reliable detection of x-ray onset, using the techniques described herein, can improve patient safety and image quality. To this end, and in accordance with an embodiment of the present disclosure, an x-ray onset detector is disclosed which provides earlier and more reliable x-ray detection to initiate the process of integrating and capturing an image, which can improve image exposure and quality while reducing radiation exposure to the patient. The disclosed detection techniques distribute physical pixels of the sensor into groups, referred to herein as superpixels, which provide rejection of temporally and spatially localized bursts of sensor noise. In some embodiments, history registers are also employed to track and remove unwanted dark current contribution to the signal, as will be explained in greater detail below.

The disclosed techniques can be implemented, for example, in a gate-level logic device, a microprocessor, an embedded processor, or a software product executable or otherwise controllable by such systems, although other embodiments will be apparent in light of this disclosure. In accordance with an embodiment, a methodology to implement these techniques includes calculating a plurality of superpixel values for each of a plurality of detection rows of a sensor. Each of the superpixel values is based on a sum of pixel values of a set of pixels associated with the superpixel value, the set of pixels selected from the detection row of a current frame of the sensor. The method also includes calculating a difference between each of the superpixel values and a corresponding stored superpixel value generated from a previous sensor frame and determining if the differences exceed a superpixel threshold value. The method further includes incrementing a hit counter in response to the determination and generating a detection signal if the hit counter exceeds a programmable hit count threshold, otherwise proceeding to process the next detection row of the current frame.

It will be appreciated that the disclosed techniques for x-ray onset detection, as described herein, may provide improved image exposure and quality while reducing radiation exposure to the patient, compared to existing techniques that suffer from false triggering, failure to generate a trigger when x-rays are present, or consuming too much of the total x-ray dose during the detection process. The techniques disclosed herein may further be implemented in hardware or software or a combination thereof. Numerous embodiments and applications will be apparent in light of this disclosure.

FIG. 1 illustrates an implementation 100 of an x-ray sensor system 120 for intraoral imaging, in accordance with an embodiment of the present disclosure. An x-ray tubehead 110 generates x-rays 115 which are directed to the intraoral region of interest 150, for example the mouth of a patient undergoing dental imaging. The x-ray sensor system 120 is located in the intraoral region, for example behind a tooth being imaged, such that the x-rays 115 pass from the tubehead 110, through the tooth, before illuminating the sensor system 120. The sensor system then forms an image which is transmitted to an imaging system 130 for display and/or data capture. In some embodiments, the transmission may be over a cable, such as USB cable 140, which runs out of the patient's mouth, although other communications schemes are possible, including wireless communications.

Figure 2:
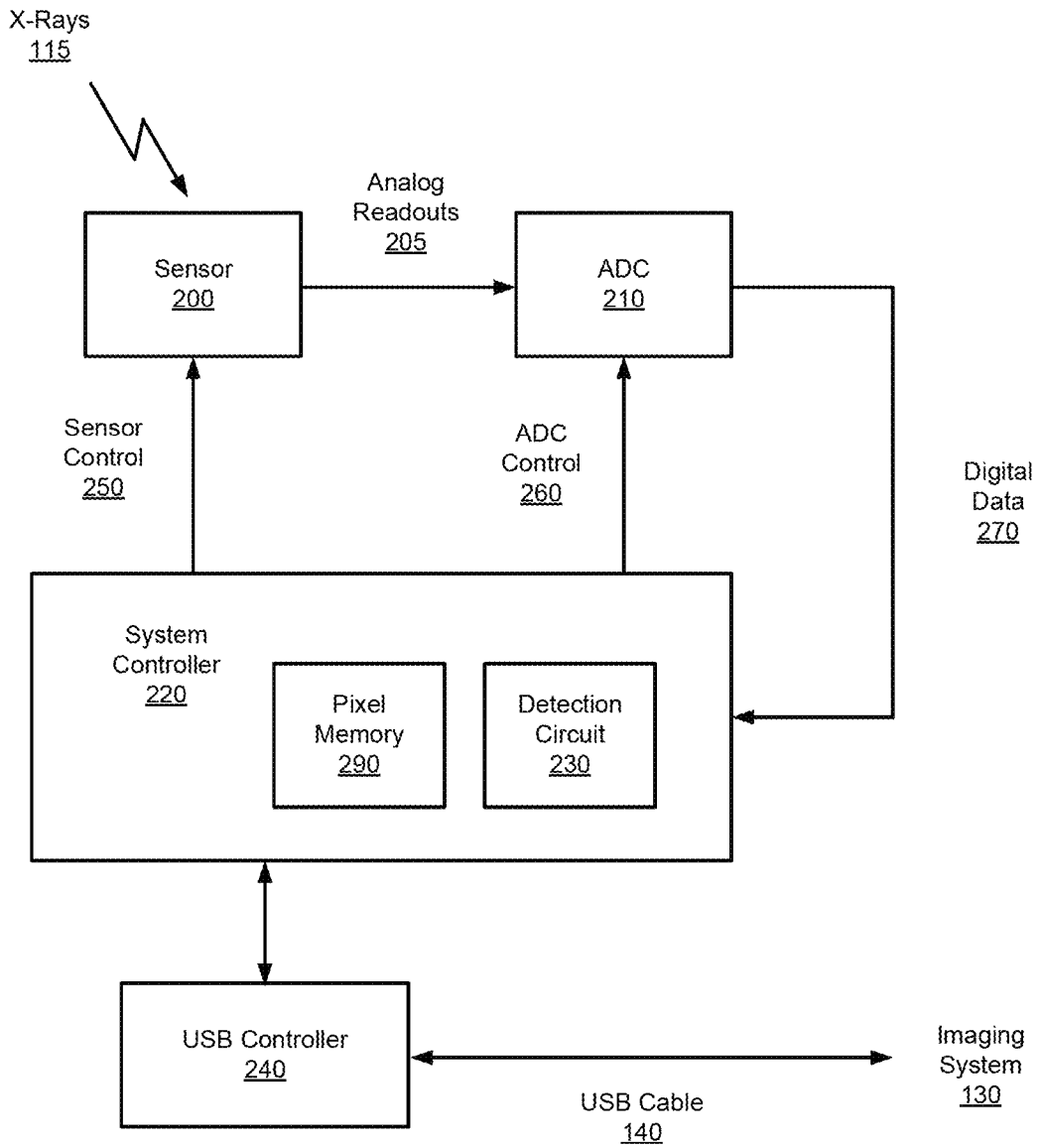
FIG. 2 is a block diagram of the x-ray sensor system of FIG. 1, configured in accordance with an embodiment of the present disclosure.

FIG. 2 is a block diagram of the x-ray sensor system 120 of FIG. 1, configured in accordance with an embodiment of the present disclosure. The x-ray sensor system 120 is shown to include a sensor 200, an analog to digital converter (ADC) 210, a system controller 220, which includes x-ray onset detection circuit 230, and a USB Controller 240.

The sensor 200 is a die that comprises an array of pixels (e.g., pixel circuits) arranged in rows and columns (e.g., M×N). In some embodiments, M and N may be in the range of 1000 to 2000. Each pixel circuit includes a photo diode and is associated with a pixel of the resulting x-ray image. The sensor 200 is configured to capture energy associated with an x-ray pulse and provide an analog signal readout 205 of the energy (e.g., integrated charge) from each pixel. The sensor may include read circuitry to read out the pixels, for example based on sensor control commands 250. The data associated with the M×N pixels generated from one x-ray pulse is referred to herein as a sensor frame.

The ADC 210 is configured to convert the analog readouts 205 to digital data 270 for use by the system controller 220 and the detection circuit 230. In one example the read out processing of the pixels and the digital conversion of the signals are accomplished in a readout integrated circuit (ROTC).

The system controller 220 is configured to generate sensor control commands 250, for example to clear the sensor 200 of data from a previous x-ray pulse, to start and stop data collection on a new x-ray pulse, to read out pixels from detection rows in a serial manner, and to read out all pixels from the sensor in a serial manner, as will be described below. The system controller 220 is also configured to control data transfer from the ADC 210 to the detection circuit 230 and to the pixel memory 290 (e.g., through ADC control 260). The system controller 220 is also configured to control data transfer from the pixel memory 290 to the USB controller 240.

In some embodiments, the detection circuit 230 is configured to detect the onset of a new x-ray pulse, based on groups of pixels (e.g., superpixels) in pre-selected detection rows of the pixel array, as will be described in greater detail below.

The USB Controller 240 is configured to transmit a frame of data from the pixel memory 290 to the imaging system 130, for example over the USB cable 140, for subsequent image generation.

Figure 3:
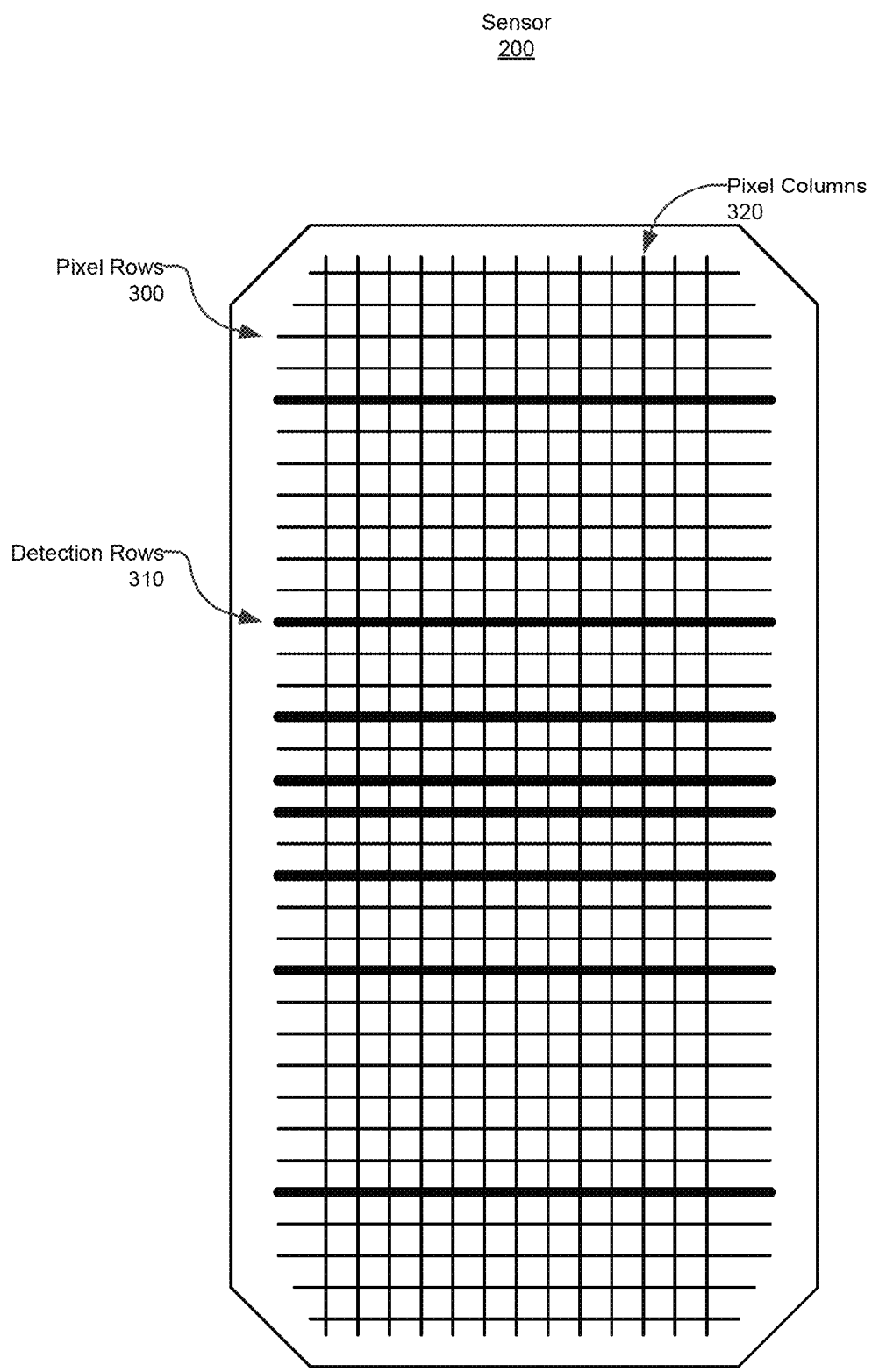
FIG. 3 illustrates pixel layout of the sensor of FIG. 2, configured in accordance with an embodiment of the present disclosure.

FIG. 3 illustrates a pixel layout of the sensor 200 of FIG. 2, configured in accordance with an embodiment of the present disclosure. In the depicted embodiment the sensor 200 has angled or chamfered corners that may shorten the length of the detection rows proximate the chamfered corners. As shown, the pixels are arranged in an array of rows 300 and columns 320, deployed on the sensor die, only a fraction of which are shown here for illustration clarity. A relatively small number of the total rows are employed as detection rows 310 (indicated by the bold lines). In some embodiments, eight detection rows may be employed.

In some embodiments, the spacing between detection rows may be constant (e.g., regular spacing), while in other embodiments the spacing may vary (e.g., irregular spacing). Some advantages of irregular spacing of the pre-selected rows include optimizing the spacing for faster access and/or biasing the detection towards a central region of the sensor. For example, as illustrated in FIG. 3, the detection rows could be spaced in a manner that provides greater density in the central region of the sensor, or in another area that may be most likely to allow x-rays to pass, to generate the detection trigger. In some embodiments, detection rows are selected to avoid impaired pixels (e.g., pixels that do not function or function in a suboptimal manner).

Figure 4:
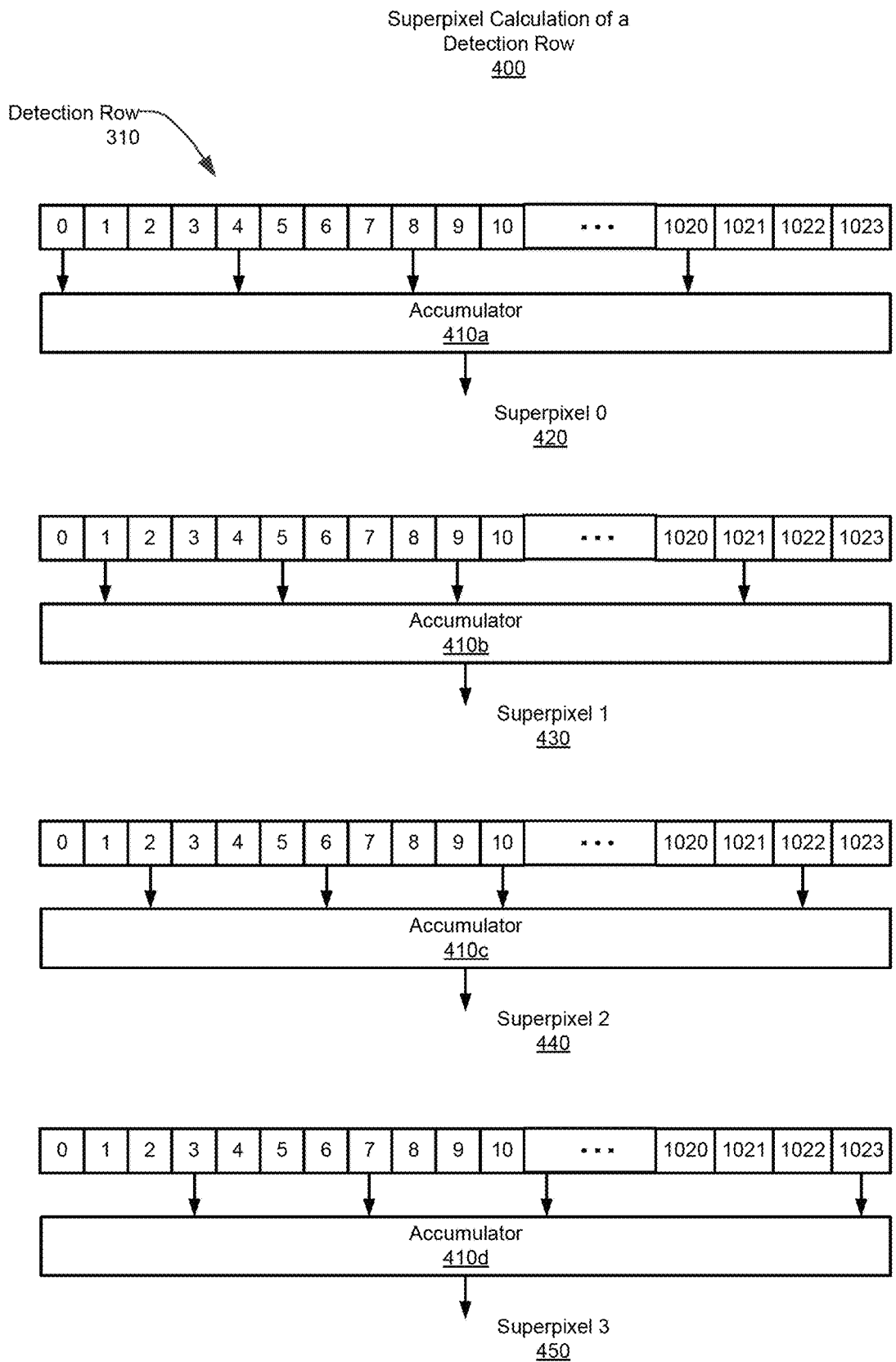
FIG. 4 illustrates superpixel calculation, in accordance with an embodiment of the present disclosure.

FIG. 4 illustrates superpixel calculation 400, in accordance with an embodiment of the present disclosure. As previously noted, superpixels are used in the detection process which will be described below in connection with FIG. 5. In this example, four superpixels 420, 430, 440, and 450, are calculated for a detection row 310 based on selected pixels from that detection row. In particular, the value of superpixel 0 420 is calculated as a sum (by accumulator 410a) of the value of every fourth pixel starting at pixel column 0 (e.g., pixels 0, 4, 8, . . . 1020). Similarly, superpixel 1 430 is calculated as a sum (by accumulator 410b) of the value of every fourth pixel starting at pixel column 1 (e.g., pixels 1, 5, 9, . . . 1021), superpixel 2 440 is calculated as a sum (by accumulator 410c) of the value of every fourth pixel starting at pixel column 2 (e.g., pixels 2, 6, 10, . . . 1022), and superpixel 3 450 is calculated as a sum (by accumulator 410d) of the value of every fourth pixel starting at pixel column 3 (e.g., pixels 3, 7, 11, . . . 1023). In this same manner, superpixels may be calculated for some or all of the other detection rows of the sensor.

In some embodiments, different spacings and offsets may be used to select the pixels from which the superpixel is calculated. In general, though, the pixels associated with a superpixel are selected as a set of the pixels of the detection row that are interleaved with the pixels that are associated with the other superpixels.

In some embodiments, the superpixels may be calculated as an average of the values of the selected pixels rather than as a sum of the values.

Figure 5:
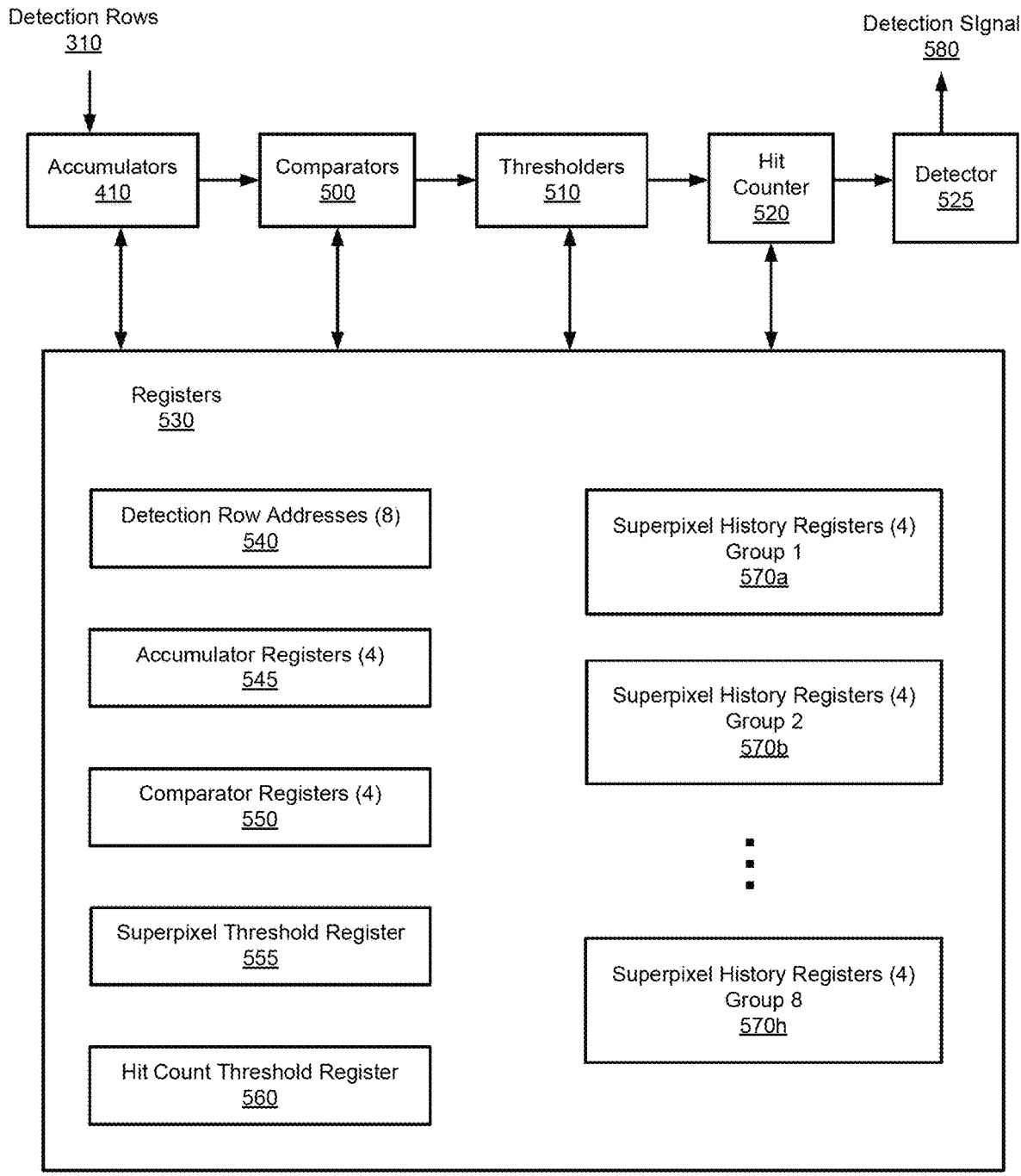
FIG. 5 is a block diagram of the detection circuit of FIG. 2, configured in accordance with an embodiment of the present disclosure.

FIG. 5 is a block diagram of the detection circuit 230 of FIG. 2, configured in accordance with an embodiment of the present disclosure. The detection circuit 230 is shown to include accumulator circuits 410, comparators 500, thresholding circuits 510, a hit counter 520, a detector 525, and set of registers 530. As previously noted, the detection circuit 230 is configured to detect the beginning of a new x-ray pulse, based on a sampling of superpixels in pre-selected detection rows of the pixel array. The process begins with the first of the detection rows and continues until a detection occurs or all detection rows of the current frame have been processed (after which the system moves to the next frame). In some embodiments, the set of registers 530 includes detection row address register 540 to specify which pixel rows are used as detection rows, allowing the selection of detection rows to be programmable. In the example illustrated in FIG. 5 there are eight detection rows 310 and eight detection row address registers 540.

The accumulator circuits 410 are configured to calculate superpixel values from a detection row of a current frame of a sensor. In the example illustrated in FIG. 5, four superpixel values are calculated for each detection row. In some embodiments, as described above, each of the superpixel values is based on a sum of pixel values of a set of pixels associated with the superpixel being calculated. Four accumulator registers 545 are configured to store the summations.

The comparators 500 are configured to calculate a difference between each of the superpixel values and a corresponding stored superpixel value that was generated from a previous frame of the sensor. In some embodiments, the difference is calculated between the current superpixel value stored in the accumulation register 545 and the previous frame superpixel value that is stored in one of the superpixel history registers 570 associated with that superpixel and detection row. As shown, there are eight groups 570a, . . . 570h of four superpixel history registers, each group associated with one of the eight detection rows. In some embodiments, the four differences are stored in the comparator registers 550.

The thresholding circuits 510 are configured to determine if the differences exceed a superpixel threshold value. In some embodiments, the superpixel threshold value is programmable and may be stored in the superpixel threshold register 555. The hit counter 520 is configured to increment a hit counter in response to the determination.

The detector 525 is configured to generate a detection signal 580 in response to a determination that the hit counter exceeds a hit count threshold. The hit count threshold determines the number of superpixel hits required in a single detection row to signify onset of an x-ray pulse. In some embodiments, the hit count threshold is programmable and may be stored in the hit count threshold register 560. In some embodiments, the hit count threshold is in the range of zero to three. The detection signal is employed to trigger the system controller to perform a reset, integration, and readout of all (or most) of the pixels of the current frame of the sensor. If the hit counter does not exceed the hit count threshold, the x-ray detector processes the next detection row in the same manner.

In some embodiments, the superpixel threshold value and/or the hit count threshold can be empirically determined or adjusted to achieve a desired balance between the probability of false alarm and the probability of detection (which is related to achieving a desired image quality). In some embodiments, these settings may be determined experimentally by taking test images of a suitable test target, using the x-ray source that will be used with the sensor system, to find the settings that provide the best detection performance.

Methodology

Figure 6:
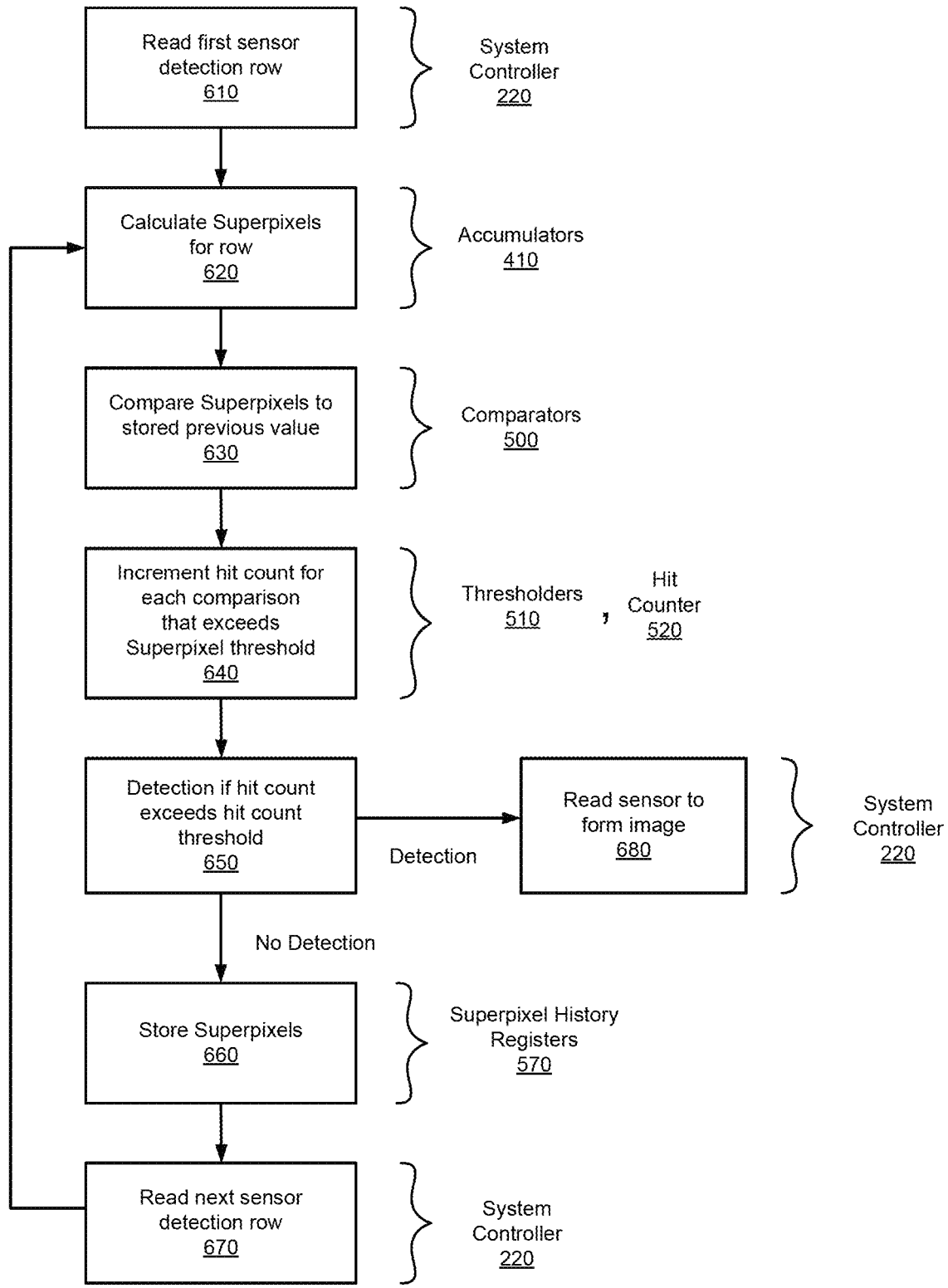
FIG. 6 is a flowchart illustrating a methodology for x-ray onset detection for an intraoral dental sensor, in accordance with an embodiment of the present disclosure.

FIG. 6 is a flowchart illustrating a methodology 600 for x-ray onset detection for an intraoral dental sensor, in accordance with an embodiment of the present disclosure. As can be seen, the example method includes a number of phases and sub-processes, the sequence of which may vary from one embodiment to another. However, when considered in the aggregate, these phases and sub-processes form a process for x-ray onset detection, in accordance with certain of the embodiments disclosed herein. These embodiments can be implemented, for example using the system architecture illustrated in FIGS. 1-5, as described above. However other system architectures can be used in other embodiments, as will be apparent in light of this disclosure. To this end, the correlation of the various functions shown in FIG. 6 to the specific components illustrated in FIGS. 1-5, is not intended to imply any structural and/or use limitations. Rather other embodiments may include, for example, varying degrees of integration wherein multiple functionalities are effectively performed by one system. Numerous variations and alternative configurations will be apparent in light of this disclosure.

As illustrated in FIG. 6, in one embodiment method 600 commences, at operation 610, by reading the pixel values from the first detection row of the current frame of the sensor. In some embodiments, the pixels values are read from the detection row serially, as previously described Next, at operation 620, superpixels are generated for that row. The values of the superpixels are calculated based on a sum of pixel values of a set of pixels, from the detection row, that are associated with the superpixel. In some embodiments, the set of pixels associated with each of the superpixels are selected from the detection row on an interleaved basis with pixels associated with other superpixels, as previously described. In some embodiments, four superpixels are employed in each detection row.

At operation 630, each of the superpixels are compared to corresponding stored superpixels generated from a previous frame of the sensor, for example as a calculated difference between the current and previous superpixel values.

At operation 640, for each difference that exceeds a superpixel threshold, a hit count is incremented.

At operation 650, if the hit count exceeds a hit count threshold, then an x-ray onset detection is triggered, and, at operation 680, pixels from the entire sensor (or a large portion thereof) are read and arranged to form an image. In some embodiments, the hit count threshold is in the range of zero to three.

If the hit count does not exceed the hit count threshold, then, at operation 660, the current superpixels are stored and, at operation 670, the next detection row of the current sensor frame is read. The process then repeats back to operation 620 for operation on that next detection row. In some embodiments, the sensor includes eight detection rows.

After all detection rows have been processed, and no detection has been triggered, the process starts over with a new sensor frame.

In some embodiments, the process may be described in more detail as follows. An initialization is performed for the first sensor frame. The initialization includes programming the addresses of the detection rows into registers 540, programming the superpixel threshold value is into register 555, and programming the hit count threshold into register 560. In some embodiments, these programmed values may be provided by the imaging system 130.

The accumulator registers 545 are cleared, and the comparator registers 550 and history registers 570 are set to a maximum negative value. This allows the first detection frame to serve as a calibration for the average dark superpixel value (or dark current) that occurs due to accumulated charge in the absence of x-ray radiation (e.g., due to heating). This can avoid the generation of a spurious detection trigger on the first frame. Because the history registers allow the system to track and remove the contribution of dark current in real time, the superpixel threshold value can be lowered without risk of false or missing triggers, reducing the radiation exposure consumed by the patient during detection. In some embodiments, the superpixel threshold value can be adjusted based on a balance between the probability of false alarm versus achieving a desired image quality. In some embodiments, the superpixel threshold value can also be adjusted based on desired radiation dosage rate.

After initialization is completed, the detection process begins for each sensor frame. For each detection row the following operations are performed. The accumulator registers 545 are cleared. The comparator registers 550 are initialized as follows. The previous superpixel values (read from the history registers 570) are loaded into the comparator registers 550 and the superpixel threshold from register 555 is added. A two's complement operation is then performed on the comparator register to generate the negative of that sum.

Next, the detection row is read, and the pixel values are added to the accumulator registers 545 and the superpixels thus formed in the accumulator registers are then added to the comparator registers 550, as previously described. A hit is signaled when the sign bit of any of the comparator registers 550 is zero. The number of hits is then compared to the hit count threshold register 560. If the number of hits exceeds the threshold, the detection signal 580 is generated, otherwise the accumulated superpixel values are stored in their corresponding history registers and the process continues with the next detection row.

Example Systems

Figure 7:
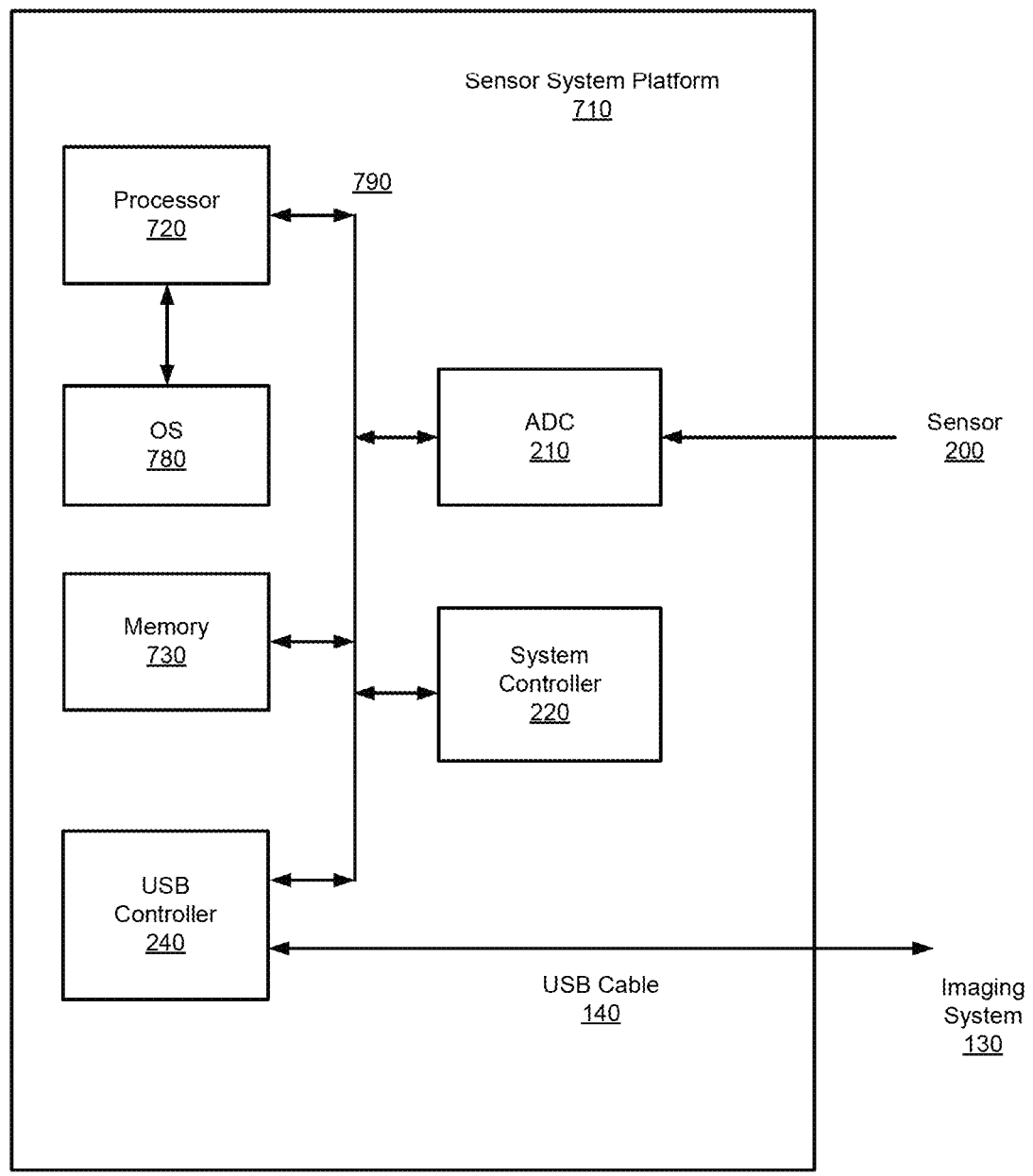
FIG. 7 is a block diagram of a platform for the x-ray sensor system, in accordance with certain embodiments of the present disclosure.

FIG. 7 is a block diagram of a platform 710 for the x-ray sensor system 120, in accordance with certain embodiments of the present disclosure. In some embodiments, the sensor system platform 710, or portions thereof, may be hosted on, or otherwise be incorporated onto a circuit board configured to fit in a capsule that is suitable for use as an intraoral dental device.

In some embodiments, platform 710 may comprise any combination of a processor 720, a memory 730, the system controller 220, the USB controller 240 (or other suitable communication interface), and the ADC 210. As can be further seen, a bus 790 is also provided to allow for communication between the various components listed above and/or other components not shown. Other componentry and functionality not reflected in the block diagram of FIG. 7 will be apparent in light of this disclosure, and it will be appreciated that other embodiments are not limited to any particular hardware configuration.

Processor 720 can be any suitable processor, and may include one or more coprocessors or controllers, such as an audio processor, a graphics processing unit, or hardware accelerator, to assist in control and processing operations associated with sensor system platform 710. In some embodiments, the processor 720 may be implemented as any number of processor cores. The processor (or processor cores) may be any type of processor, such as, for example, a microprocessor, an embedded processor, a digital signal processor (DSP), a graphics processor (GPU), a network processor, a field programmable gate array or other device configured to execute code. The processors may be multi-threaded cores in that they may include more than one hardware thread context (or "logical processor") per core. Processor 720 may be implemented as a complex instruction set computer (CISC) or a reduced instruction set computer (RISC) processor.

Memory 730 can be implemented using any suitable type of digital storage including, for example, flash memory and/or random access memory (RAM). In some embodiments, the memory 730 may include various layers of memory hierarchy and/or memory caches as are known to those of skill in the art. Memory 730 may be implemented as a volatile memory device such as, but not limited to, a RAM, dynamic RAM (DRAM), or static RAM (SRAM) device.

Processor 720 may be configured to execute an Operating System (OS) 780 which may comprise any suitable operating system, such as Google Android (Google Inc., Mountain View, CA), Microsoft Windows (Microsoft Corp., Redmond, WA), Apple OS X (Apple Inc., Cupertino, CA), Linux, or a real-time operating system (RTOS). As will be appreciated in light of this disclosure, the techniques provided herein can be implemented without regard to the particular operating system provided in conjunction with sensor system platform 710, and therefore may also be implemented using any suitable existing or subsequently-developed systems or platforms.

It will be appreciated that in some embodiments, some of the various components of sensor system platform 710 may be combined or integrated in a system-on-a-chip (SoC) architecture. In some embodiments, the components may be hardware components, firmware components, software components or any suitable combination of hardware, firmware or software.

Processor 720, which may be implemented as an FPGA in some embodiments, is configured to perform the functions of system controller 220 including detection circuit 230, as described previously.

Various embodiments of sensor system platform 710 may be implemented using hardware elements, software elements, or a combination of both. Examples of hardware elements may include processors, microprocessors, circuits, circuit elements (for example, transistors, resistors, capacitors, inductors, and so forth), integrated circuits, application-specific integrated circuits (ASICs, or other purpose-built semiconductors), programmable logic devices, digital signal processors, field programmable gate arrays (FPGAs), logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

The various embodiments disclosed herein can be implemented in various forms of hardware, software, firmware, and/or special purpose processors. For example, in one embodiment at least one non-transitory computer readable storage medium has instructions encoded thereon that, when executed by one or more processors, causes one or more of the methodologies disclosed herein to be implemented. Other componentry and functionality not reflected in the illustrations will be apparent in light of this disclosure, and it will be appreciated that other embodiments are not limited to any particular hardware or software configuration. Thus, in other embodiments sensor system platform 710 may comprise additional, fewer, or alternative subcomponents as compared to those included in the example embodiment of FIG. 7.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still cooperate or interact with each other.

The aforementioned non-transitory computer readable medium may be any suitable medium for storing digital information, such as a hard drive, a server, a flash memory, and/or random access memory (RAM), or a combination of memories. In alternative embodiments, the components and/or modules disclosed herein can be implemented with hardware, including gate-level logic such as a field-programmable gate array (FPGA), or alternatively, a purpose-built semiconductor such as an application-specific integrated circuit (ASIC). In some embodiments, the hardware may be modeled or developed using hardware description languages such as, for example Verilog or VHDL. Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Some examples may be implemented, for example, using a machine-readable medium or article which may store an instruction or a set of instructions that, if executed by a machine, may cause the machine to perform a method and/or operations in accordance with an embodiment provided herein. Such a machine may include, for example, any suitable processing platform, computing platform, computing device, processing device, computing system, processing system, computer, process, or the like, and may be implemented using any suitable combination of hardware and/or software. The machine-readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CD-RW) memory, optical disk, magnetic media, magneto-optical media, removable memory cards or disks, flash drives, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

The terms "circuit" or "circuitry," as used in any embodiment herein, are functional structures that include hardware, or a combination of hardware and software, and may comprise, for example, singly or in any combination, hardwired circuitry, programmable circuitry such as computer processors comprising one or more individual instruction processing cores, state machine circuitry, and/or gate level logic. The circuitry may include a processor and/or controller programmed or otherwise configured to execute one or more instructions to perform one or more operations described herein. The instructions may be embodied as, for example, an application, software, firmware, or one or more embedded routines configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads or parallel processes in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit (IC), an application-specific integrated circuit (ASIC), a system-on-a-chip (SoC), computers, and other processor-based or functional systems. Other embodiments may be implemented as software executed by a programmable device. In any such hardware cases that include executable software, the terms "circuit" or "circuitry" are intended to include a combination of software and hardware such as a programmable device or a processor capable of executing the software. As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is a an x-ray detector comprising: an accumulator circuit configured to calculate a plurality of superpixel values, each of the superpixel values based on a sum of pixel values of a set of pixels associated with the superpixel value, the set of pixels selected from a detection row of a current frame of a sensor; a comparator circuit configured to calculate a difference between each of the plurality of superpixel values and a corresponding stored superpixel value generated from a previous frame of the sensor; a thresholding circuit configured to determine if the differences exceed a superpixel threshold value and to increment a hit counter in response to the determination; and a detection circuit configured to generate a detection signal in response to a determination that the hit counter exceeds a hit count threshold.

Example 2 includes the x-ray detector of Example 1, wherein the detection row is a first detection row, and the x-ray detector is configured to process a second detection row, of a plurality of detection rows, in response to a determination that the hit counter does not exceed the hit count threshold.

Example 3 includes the x-ray detector of Examples 1 or 2, wherein the plurality of detection rows comprises eight detection rows.

Example 4 includes the x-ray detector of any of Examples 1-3, wherein the set of pixels associated with each of the plurality of superpixel values is selected as a set of the pixels of the detection row that are interleaved with pixels associated with another of the plurality of superpixels values.

Example 5 includes the x-ray detector of any of Examples 1-4, wherein the plurality of superpixels comprises four superpixels and the hit count threshold is in the range of zero to three.

Example 6 includes the x-ray detector of any of Examples 1-5, wherein the frame of the sensor comprises a number of non-detection rows in the range of 1000 to 2000, and the detection rows are selected to avoid impaired pixels.

Example 7 includes the x-ray detector of any of Examples 1-6, wherein the detection rows are interleaved with the non-detection rows and the detection rows are distributed more densely near a central region of the sensor.

Example 8 includes the x-ray detector of any of Examples 1-7, wherein the detection signal is employed to trigger an integration and readout of the values of the pixels of the detection rows and values of pixels of non-detection rows of the current frame of the sensor.

Example 9 is a computer program product including one or more non-transitory machine-readable mediums encoded with instructions that when executed by one or more processors cause a process to be carried out for introral x-ray detection, the process comprising: calculating a plurality of superpixel values, each of the superpixel values based on a sum of pixel values of a set of pixels associated with the superpixel value, the set of pixels selected from a detection row of a current frame of a sensor; calculating a difference between each of the plurality of superpixel values and a corresponding stored superpixel value generated from a previous frame of the sensor; determining if the differences exceed a superpixel threshold value; incrementing a hit counter in response to the determination; and generating a detection signal in response to a determination that the hit counter exceeds a hit count threshold.

Example 10 includes the computer program product of Example 9, wherein the detection row is a first detection row, and the process further comprises repeating the process on a second detection row, of a plurality of detection rows, in response to a determination that the hit counter does not exceed the hit count threshold.

Example 11 includes the computer program product of Examples 9 or 10, wherein the plurality of detection rows comprises eight detection rows.

Example 12 includes the computer program product of any of Examples 9-11, wherein the process further comprises selecting the set of pixels associated with each of the plurality of superpixel values as a set of the pixels of the detection row that are interleaved with pixels associated with another of the plurality of superpixels values.

Example 13 includes the computer program product of any of Examples 9-12, wherein the plurality of superpixels comprises four superpixels and the hit count threshold is in the range of zero to three.

Example 14 includes the computer program product of any of Examples 9-13, wherein the frame of the sensor comprises a number of non-detection rows in the range of 1000 to 2000 and the detection rows are interleaved with the non-detection rows and the detection rows are distributed more densely near a central region of the sensor.

Example 15 includes the computer program product of any of Examples 9-14, wherein the process further comprises triggering an integration and readout of the values of the pixels of the detection rows and values of pixels of non-detection rows of the current frame of the sensor, in response to the detection signal.

Example 16 is a method for intraoral x-ray detection, the method comprising: calculating, by a processor-based system, a plurality of superpixel values, each of the superpixel values based on a sum of pixel values of a set of pixels associated with the superpixel value, the set of pixels selected from a detection row of a current frame of a sensor; calculating, by the processor-based system, a difference between each of the plurality of superpixel values and a corresponding stored superpixel value generated from a previous frame of the sensor; determining, by the processor-based system, if the differences exceed a superpixel threshold value; incrementing, by the processor-based system, a hit counter in response to the determination; and generating, by the processor-based system, a detection signal in response to a determination that the hit counter exceeds a hit count threshold.

Example 17 includes the method of Example 16, wherein the detection row is a first detection row, and the method further comprises repeating the process on a second detection row, of a plurality of detection rows, in response to a determination that the hit counter does not exceed the hit count threshold.

Example 18 includes the method of Examples 16 or 17, further comprising selecting the set of pixels associated with each of the plurality of superpixel values as a set of the pixels of the detection row that are interleaved with pixels associated with another of the plurality of superpixels values.

Example 19 includes the method of any of Examples 16-18, wherein the plurality of superpixels comprises four superpixels and the hit count threshold is in the range of zero to three.

Example 20 includes the method of any of Examples 16-19, further comprising triggering an integration and readout of the values of the pixels of the detection rows and values of pixels of non-detection rows of the current frame of the sensor, in response to the detection signal.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not by this detailed description, but rather by the claims appended hereto. Future filed applications claiming priority to this application may claim the disclosed subject matter in a different manner and may generally include any set of one or more elements as variously disclosed or otherwise demonstrated herein.

What is claimed is:

1. An x-ray detector comprising:
an accumulator circuit configured to calculate a plurality of superpixel values, each of the superpixel values based on a sum of pixel values of a set of pixels associated with the superpixel value, the set of pixels selected from a detection row of a current frame of a sensor, wherein the set of pixels associated with each of the plurality of superpixel values is selected as a set of the pixels of the detection row that are interleaved with pixels associated with another of the plurality of superpixels values;

a comparator circuit configured to calculate a difference between each of the plurality of superpixel values and a corresponding stored superpixel value generated from a previous frame of the sensor;

a thresholding circuit configured to determine if the differences exceed a superpixel threshold value and to increment a hit counter in response to the determination; and a detection circuit configured to generate a detection signal in response to a determination that the hit counter exceeds a hit count threshold.

2. The x-ray detector of claim 1, wherein the detection row is a first detection row, and the x-ray detector is configured to process a second detection row, of a plurality of detection rows, in response to a determination that the hit counter does not exceed the hit count threshold.

3. The x-ray detector of claim 2, wherein the plurality of detection rows comprises eight detection rows.

4. The x-ray detector of claim 1, wherein the plurality of superpixels comprises four superpixels and the hit count threshold is in the range of zero to three.

5. The x-ray detector of claim 1, wherein the frame of the sensor comprises a number of non-detection rows in the range of 1000 to 2000, and the detection rows are selected to avoid impaired pixels.

6. The x-ray detector of claim 5, wherein the detection rows are interleaved with the non-detection rows and the detection rows are distributed more densely near a central region of the sensor.

7. The x-ray detector of claim 1, wherein the detection signal is employed to trigger an integration and readout of the values of the pixels of the detection rows and values of pixels of non-detection rows of the current frame of the sensor.

8. A computer program product including one or more non-transitory machine-readable mediums encoded with instructions that when executed by one or more processors cause a process to be carried out for intraoral x-ray detection, the process comprising:

calculating a plurality of superpixel values, each of the superpixel values based on a sum of pixel values of a set of pixels associated with the superpixel value, the set of pixels selected from a detection row of a current frame of a sensor, wherein selecting the set of pixels associated with each of the plurality of superpixel values as a set of the pixels of the detection row that are interleaved with pixels associated with another of the plurality of superpixels values;

calculating a difference between each of the plurality of superpixel values and a corresponding stored superpixel value generated from a previous frame of the sensor;

determining if the differences exceed a superpixel threshold value;

incrementing a hit counter in response to the determination; and generating a detection signal in response to a determination that the hit counter exceeds a hit count threshold.

9. The computer program product of claim 8, wherein the detection row is a first detection row, and the process further comprises repeating the process on a second detection row, of a plurality of detection rows, in response to a determination that the hit counter does not exceed the hit count threshold.

10. The computer program product of claim 9, wherein the plurality of detection rows comprises eight detection rows.

11. The computer program product of claim 8, wherein the plurality of superpixels comprises four superpixels and the hit count threshold is in the range of zero to three.

12. The computer program product of claim 8, wherein the frame of the sensor comprises a number of non-detection rows in the range of 1000 to 2000 and the detection rows are interleaved with the non-detection rows and the detection rows are distributed more densely near a central region of the sensor.

13. The computer program product of claim 8, wherein the process further comprises triggering an integration and readout of the values of the pixels of the detection rows and values of pixels of non-detection rows of the current frame of the sensor, in response to the detection signal.

14. A method for intraoral x-ray detection, the method comprising:

calculating, by a processor-based system, a plurality of superpixel values, each of the superpixel values based on a sum of pixel values of a set of pixels associated with the superpixel value, the set of pixels selected from a detection row of a current frame of a sensor;

selecting the set of pixels associated with each of the plurality of superpixel values as a set of the pixels of the detection row that are interleaved with pixels associated with another of the plurality of superpixels values;

calculating, by the processor-based system, a difference between each of the plurality of superpixel values and a corresponding stored superpixel value generated from a previous frame of the sensor;

determining, by the processor-based system, if the differences exceed a superpixel threshold value;

incrementing, by the processor-based system, a hit counter in response to the determination; and generating, by the processor-based system, a detection signal in response to a determination that the hit counter exceeds a hit count threshold.

15. The method of claim 14, wherein the detection row is a first detection row, and the method further comprises repeating the process on a second detection row, of a plurality of detection rows, in response to a determination that the hit counter does not exceed the hit count threshold.

16. The method of claim 14, wherein the plurality of superpixels comprises four superpixels and the hit count threshold is in the range of zero to three.

17. The method of claim 14, further comprising triggering an integration and readout of the values of the pixels of the detection rows and values of pixels of non-detection rows of the current frame of the sensor, in response to the detection signal.

* * * * *